United States Patent
Burdett et al.

(10) Patent No.: US 7,711,506 B2
(45) Date of Patent: May 4, 2010

(54) SENSOR CALIBRATION

(75) Inventors: Alison Burdett, Oxon (GB); Paul Padden, Oxon (GB)

(73) Assignee: Bio-Nano Sensium Technologies Limited, London (GB)

( * ) Notice: Subject to any disclaimer, the term of this patent is extended or adjusted under 35 U.S.C. 154(b) by 210 days.

(21) Appl. No.: 11/919,998

(22) PCT Filed: May 16, 2006

(86) PCT No.: PCT/GB2006/050111
§ 371 (c)(1),
(2), (4) Date: Nov. 7, 2007

(87) PCT Pub. No.: WO2006/123186
PCT Pub. Date: Nov. 23, 2006

(65) Prior Publication Data
US 2009/0093985 A1  Apr. 9, 2009

(30) Foreign Application Priority Data
May 17, 2005 (GB) .................................. 0509934

(51) Int. Cl.
*G01D 18/00* (2006.01)

(52) U.S. Cl. ...................................................... 702/91
(58) Field of Classification Search .................. 702/85, 702/91, 104; 600/485
See application file for complete search history.

(56) References Cited

U.S. PATENT DOCUMENTS

| 4,894,339 A | 1/1990 | Hanazato et al. |
| 6,175,752 B1 | 1/2001 | Say et al. |
| 7,344,500 B2 * | 3/2008 | Talbot et al. ................ 600/365 |

FOREIGN PATENT DOCUMENTS

| WO | WO 2005/041766 A | 5/2005 |
| WO | WO 2006/024671 A | 3/2006 |

* cited by examiner

*Primary Examiner*—Bryan Bui
(74) *Attorney, Agent, or Firm*—Arent Fox LLP

(57) ABSTRACT

A method of calibrating a sensor system comprising a disposable sensor and a computer device, both the sensor and the computer device having circuitry for facilitating the transmission of data between them via a wireless communication link. The method comprises storing a final value of a monitored parameter obtained using a first disposable sensor, or some other value derivable from said final value, in a memory of the computer device, and calibrating the system for a new disposable sensor using said final value or said other value.

18 Claims, 4 Drawing Sheets

SENSOR CALIBRATION

FIELD OF THE INVENTION

The present invention relates to the calibration of sensors and in particular, though not necessarily, to the calibration of body wearable medical biosensors.

BACKGROUND TO THE INVENTION

A "biosensor" has been defined as an analytical device incorporating a biological or biologically-derived sensing element either integrated within or intimately associated with a physicochemical transducer. Biosensors are generally designed to produce either discrete or continuous digital electronic signals that are proportional to a single analyte or a related group of analytes, although the provision of analogue signals should not be excluded.

There are many areas of application for biosensors including for example environmental sensing, chemical production, and food and drink production and preparation. One area of application that has attracted a great deal of interest however is that of medical diagnostics, monitoring, and treatment. The following discussion addresses primarily these medical applications, although it will be appreciated that the problems and solutions considered may also have non-medical applications.

A typical example of a medical monitoring biosensor is the glucose biosensor that is designed to produce an electrical signal indicative of the level of glucose present in a user's (i.e. the patient's) system. Today's glucose biosensors tend to be based around the concept of immobilising an enzyme or other reagent on the surface of an electrode to provide what is essentially a pH detector. When the reagent is exposed to a sample obtained from the patient, e.g. a drop of blood, the electrical output of the device indicates the pH value of the sample and hence indirectly the level of glucose. Commercially available glucose biosensors tend to be handheld type devices which accept a disposable test strip or element.

A user may be expected, e.g. in the case of a diabetes sufferer, to test his or her glucose level several times a day in order to provide a sufficient degree of feedback to allow intervention if the detected level deviates significantly from the "normal" level. Biosensors of this type have their limitations. In particular, due to the need for users to prick their skin to obtain a blood sample, and to then perform a short but still inconvenient test procedure using the biosensor, users may not perform the test as often as required. Skin pricking is also painful and, over the long term, can result in serious skin damage. These problems apply equally to other types of biosensors which measure analytes present in blood and thus require the provision of blood samples; for example the measurement of oxygen, lactate, nitric acid, creatine, dopamine, serotonin, noradrenaline. The measurement of these analytes is useful in the understanding and monitoring of diseases as diverse as heart disease, rheumatoid arthritis and Parkinsons disease.

Substantially non-invasive biosensors have been proposed. These might be wearable on the skin, making contact with interstitial fluid drawn through the upper layers of the skin by tiny micro-needles to provide continuous monitoring. However, the nature of such biosensors, being exposed to dirt and water and being subject to aggressive physical contact, e.g. via a user's clothes, is likely to require that the sensors be disposable, being used for only a relatively short period of time. Power consumption and battery capacity may also make disposability the preferred option. Two-part biosensor systems have been proposed that use a radio frequency wireless link to transfer data between a wearable biosensor and a central controller. Such a controller might be carried in a user's pocket or worn on his or her belt. The controller displays measured results on a display screen and may log historical data.

A typical biosensor system requires calibration of a biosensor prior to use in order to compensate for device variations and to ensure the accuracy of results. This might require, for example, measuring a parameter of a known fluid sample. In the case of a glucose biosensor, a user might be provided with a vial containing liquid with a known glucose concentration, the user breaking a seal and pouring the liquid onto the active sensor surface to calibrate the system. This approach is both time consuming and inconvenient for the user, and requires that the user be provided with a fresh vial for every biosensor.

U.S. Pat. No. 6,441,747 describes a wireless programmable system for medical monitoring that includes a base unit designed to communicate with a plurality of worn biosensor transceivers.

US2004/0096959 describes a glucose sensor in the form of a skin patch having a microneedle which penetrates the skin to draw out interstitial fluid. Glucose measurements are sent from the patch to a remote display unit, over a wireless link.

Other documents relevant to this field are:
IEEE Trans Biomed Eng, vol 35, no 7, July 1988, p 526-532;
Diabetes Technol Ther, vol 1, no 3, 1999, p 261-6;
Med Eng Phys, vol 18, no 8, 1996 December, p 632-40;
US20010041831; and
WO2000067633.

SUMMARY OF THE INVENTION

The present invention springs from a recognition that the two-part sensor system provides a means for calibrating new sensors by carrying data forward from an old sensor. Calibration with some control sample is not required for each and every sensor.

According to a first aspect of the present invention there is provided a method of calibrating a sensor system comprising a disposable sensor and a computer device, both the sensor and the computer device having circuitry for facilitating the transmission of data between them via a wireless communication link, the method comprising:

storing a final value of a monitored parameter obtained using a first disposable sensor, or some other value derivable from said final value, in a memory of the computer device; and calibrating the system for a new disposable sensor using said final value or said other value.

Said final value or other value is used to compute a calibration factor for the new sensor. This factor may be a constant used to evaluate the parameter being monitored from a measured value. The final value or said other value, or said calibration factor, may be sent from the computer device to the disposable sensor where evaluation of the monitored parameter, or a part of the evaluation, is carried out at the sensor. On the other hand, the final value or said other value, or said calibration factor, may be retained at the computer device where evaluation of the monitored parameter, or a part of the evaluation, is carried out at the computer device.

The invention is particularly applicable to a medical sensor system, where the sensor is wearable. The sensor may be a pH sensor. More particularly the sensor may be an ISFET based biosensor, where the measured value is the gate-source voltage of the ISFET or the voltage or current through the drain/source.

According to a second aspect of the present invention there is provided a sensor system comprising:

a disposable sensor, at least a portion of which is arranged in use to come into contact with a substance; and a computer device, both the sensor and the computer device having circuitry for facilitating the transmission of data between them via a wireless communication link, the computer device further comprising a memory for storing a final value of a parameter being monitored, or some other value driveable from said final value, for a first disposable sensor, and processing means for using said final or other value to calibrate a new disposable sensor.

DETAILED DESCRIPTION OF CERTAIN EMBODIMENTS OF THE INVENTION

Figure 1:
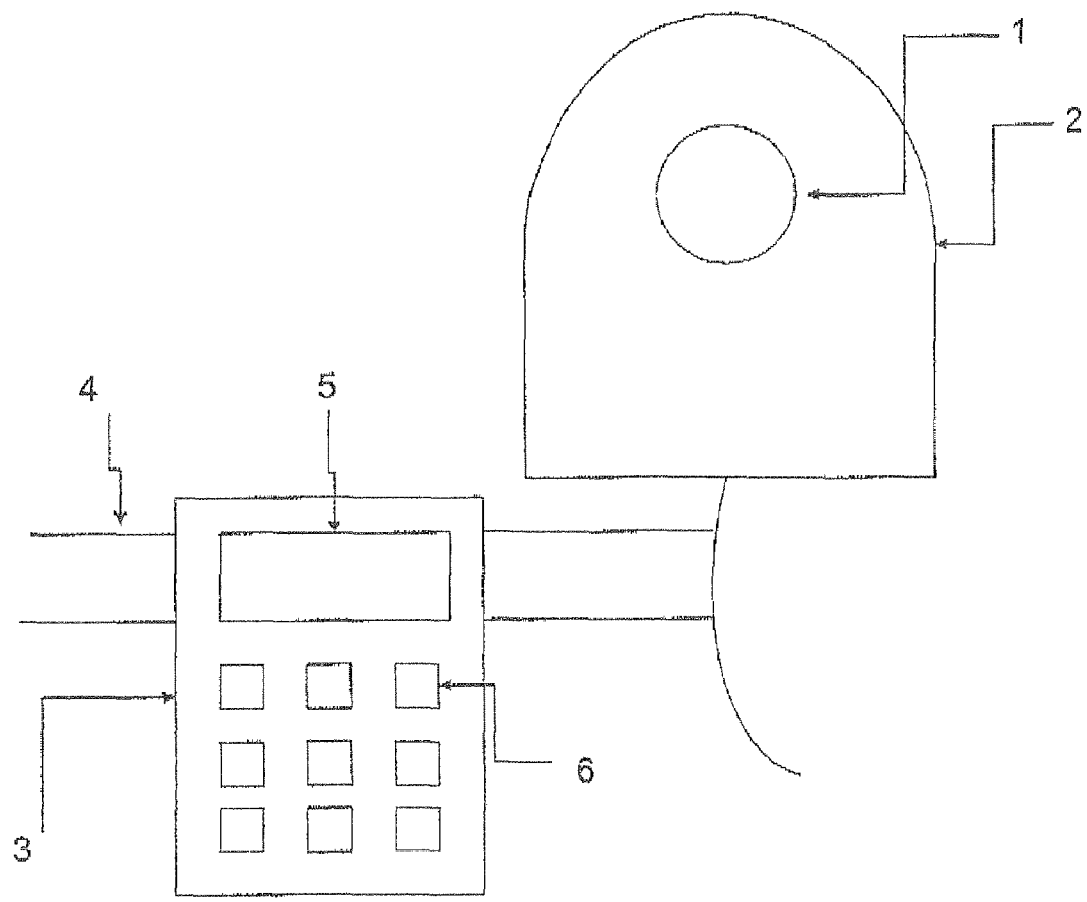
FIG. 1 illustrates schematically a sensor system carried by a user.

There is illustrated in FIG. 1 a human wearable sensor system. This may be suitable, for example, for continuously monitoring the glucose level of a user suffering from diabetes. The system comprises two main components: a disposable sensor 1 in the form of a patch that is affixed to a user's skin, e.g. on the arm 2, and a controller 3 which, in the example shown, is attached to the user's belt 4. The controller 3 comprises a user interface including a liquid crystal display (LCD) 5 and a keypad 6.

Figure 2:
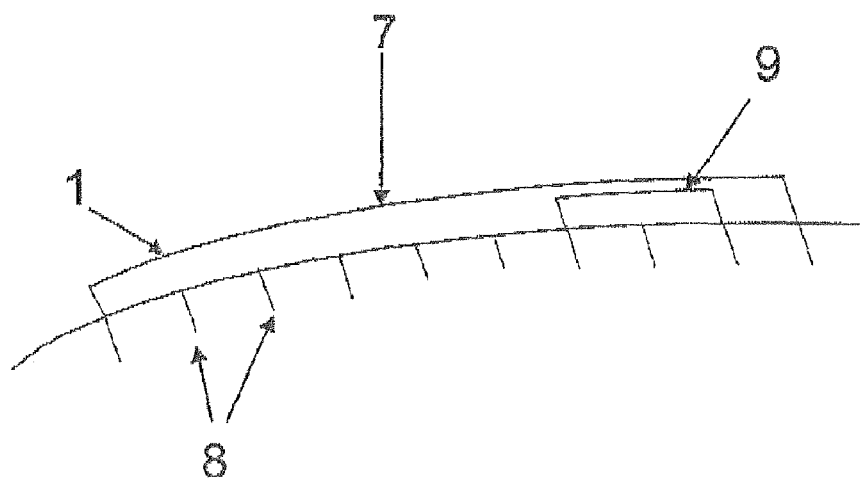
FIG. 2 illustrates in cross-section a biosensor patch of the system of FIG. 1, attached to the user's skin.

FIG. 2 shows a cross-sectional view of the sensor patch 1, affixed to the user's skin. The patch 1 comprises a flexible carrier 7 which may be of a plastics or fabric material, or of a metal foil. The underside of the carrier may be coated with an adhesive to allow the patch to be fixed to the skin, if the carrier is itself not sufficiently "sticky". Projecting from the underside of the patch is an array, e.g. 100, of micro-needles 8. These are typically 1-1000 micrometers in diameter, and have the form of a hypodermic needle, i.e. with a passage extending through the middle thereof, the passage being open at the bottom tip. When the patch is pressed against the skin, the needles penetrate the surface of the skin down to the cutaneous level, allowing interstitial fluid to be conducted up through the needles into the patch. The relatively small size of the needles does not cause the user any pain, and apparently results in little or no long term skin damage. [See "ENDOPORATOR" (EU FP5 IST-2001-33141)].

Some means (not shown in the Figures) is provided for conducting fluid from the needles to an active biosensor component 9. This means could be, for example, a capillary tube or set of tubes, or a wick of some kind. The biosensor component 9 may be, for example, an ion sensitive field effect transistor (ISFET) based biosensor of the type described in "Weak Inversion ISFETs for ultra low power biochemical sensing and real time analysis", Leila Shephard and Chris Toumazou, Sensors and Actuators 2004, Elsevier BV. Regardless of the type of biosensor used, the sensor will provide at an output an electrical signal that is indicative of the glucose level in the sampled fluid.

Figure 3:
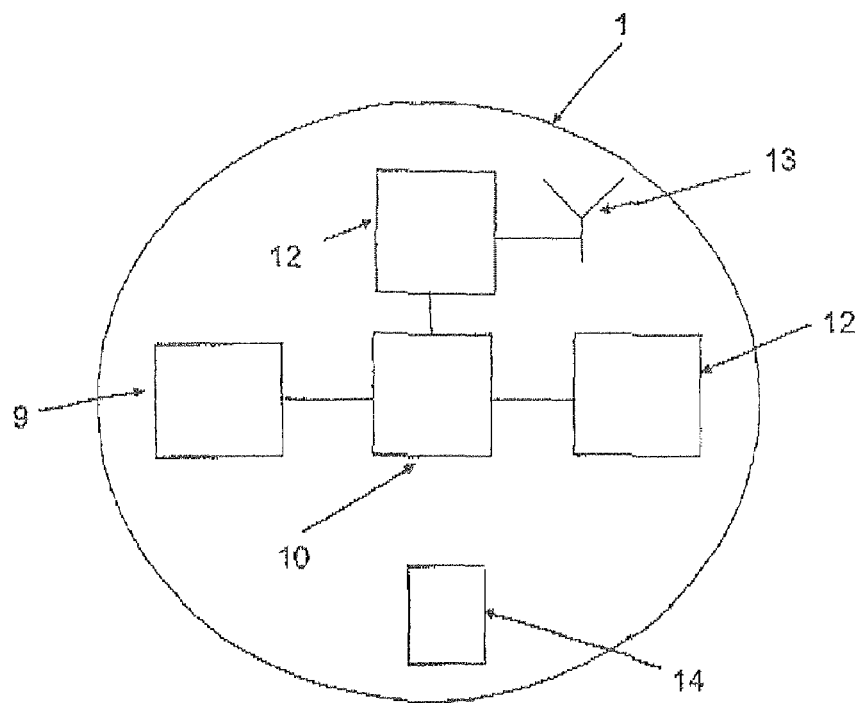
FIG. 3 illustrates schematically, electronic components of the biosensor of FIG. 2.

Referring now to FIG. 3, the various components of the sensor patch 1 are illustrated schematically. A processor 10 has an input coupled to the output of the biosensor 9. The processor 10 is also coupled to a memory 11 and to a radio frequency transceiver 12. The transceiver is coupled to a radio frequency antenna 13. Whilst the various components 9-13 may be provided as discrete components, in a preferred implementation these are all integrated onto a single piece of silicon. A power source 14 is provided to power the various electrical components. This could be, for example, a battery. For a new patch, the battery may be activated by the user tearing a strip from the patch, the strip isolating the battery terminals from the power supply leads.

Due to the need for small size and low cost, driven in turn by the requirement to provide a disposable patch, the complexity of the patch electronics must be kept to an absolute minimum. This objective also goes a long way towards satisfying the requirement for extremely low power consumption. Very little processing is typically carried out on the raw monitored data by the patch electronics. The raw data may be merely digitised by the processor 10 and transmitted by the transceiver 12 over the wireless link, to the controller 3.

Figure 4:
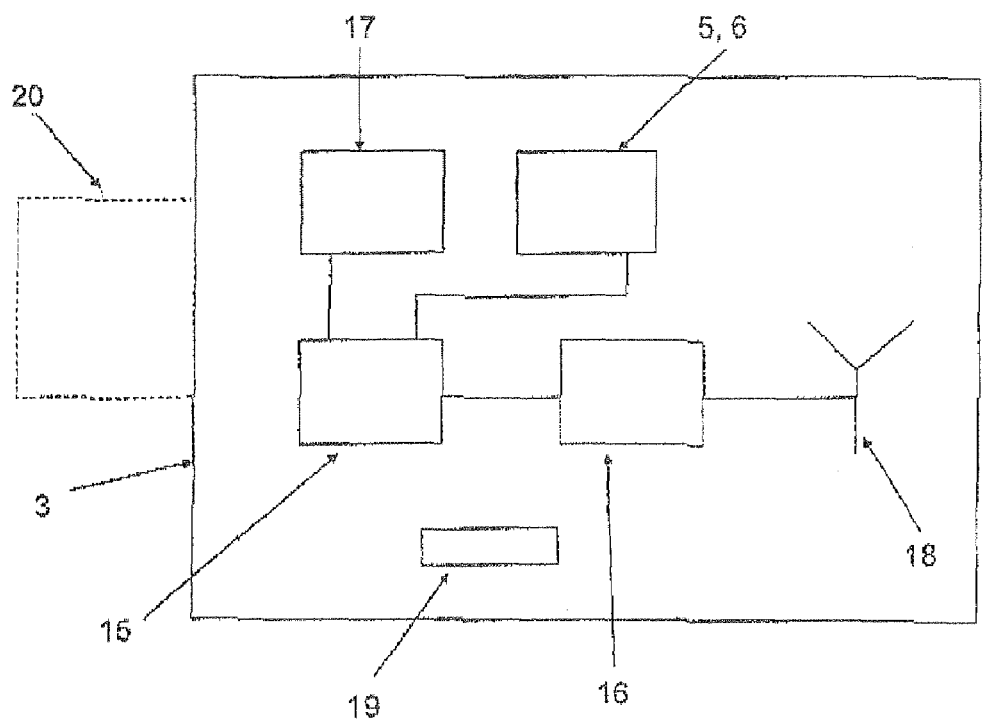
FIG. 4 illustrates schematically a controller of the system of FIG. 1.

The main components of the controller 3 are illustrated schematically in FIG. 4. These include a microprocessor 15 coupled to a transceiver 16, a memory 17, and the user interface 5,6. The transceiver 16 is coupled to an antenna 18. These components are powered by a battery 19. It will be appreciated that the size and power consumption requirements placed on the controller are significantly less than those placed on the sensor 1. The approach used in this system is therefore to carry out most of the processing on the monitored signal at the controller 3. This will make use of processing routines stored as program code in the memory 17 and accessed by the processor 15.

The sensor system is configurable to some extent by the user, via the user interface of the controller 3. For example, when a user activates a new sensor patch, he or she may be able to reset the calibration process by entering a blood glucose reading obtained using a finger prick (blood) test, overriding the default "carry-forward" calibration process described below.

Figure 5:
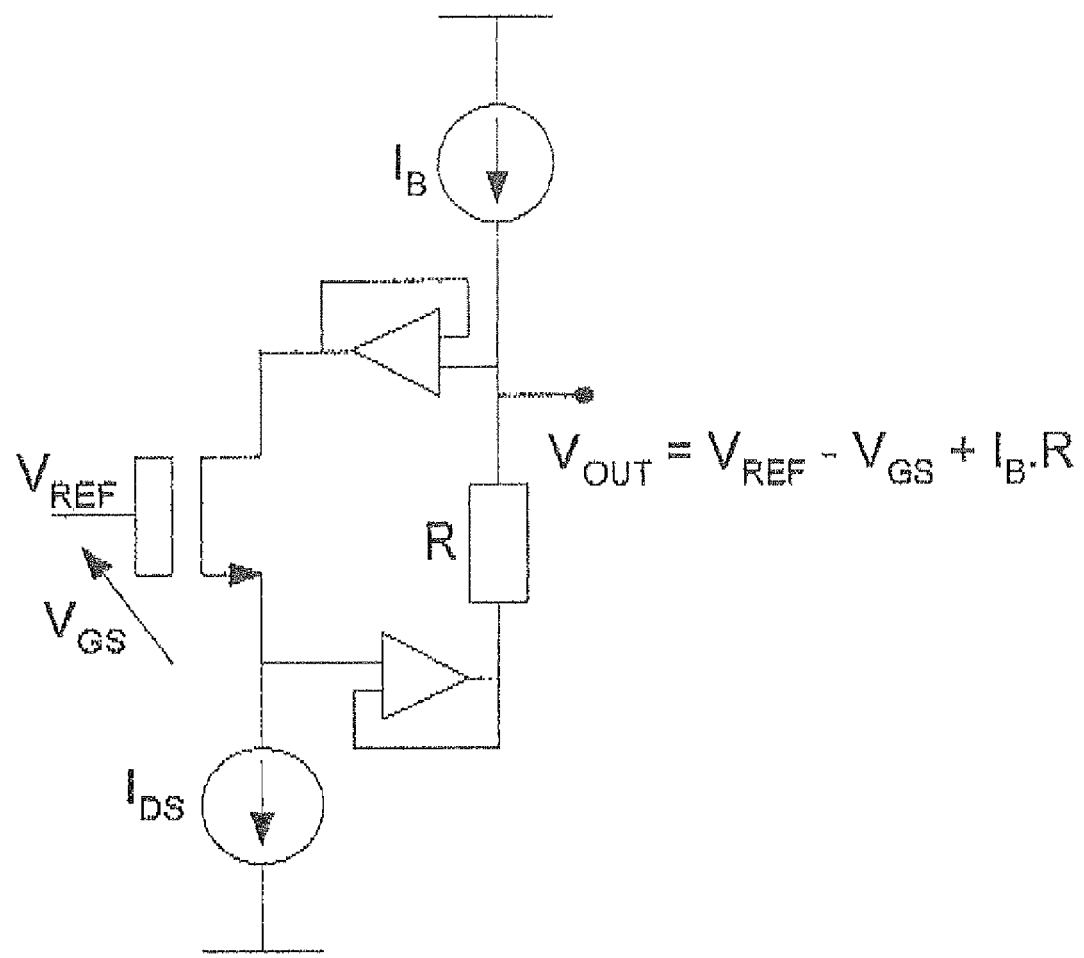
FIG. 5 illustrates an electrical circuit of the biosensor patch of FIG. 2, including an ISFET.

Considering further the ISFET of the biosensor patch, a typical ISFET and associated biasing and measuring circuitry is illustrated schematically in FIG. 5. A change in the pH of a solution in contact with the ion-sensitive gate of the ISFET causes a change in the ISFET threshold voltage. By detecting changes in the threshold voltage, the pH value may thus be measured. [See: 'ISFET sensor coupled with CMOS read-out circuit microsystem', L. Ravezzi and P. Conchi, IEE Electronics Letters, 1998, 34(23), pp. 2234-2235.] The ISFET is biased in the linear region, thus the drain current is:

$$I_{DS} = K[(V_{GS} - V_T) - (V_{DS}/2)]V_{DS} \approx K(V_{GS} - V_T)V_{DS} \quad (1)$$

where $I_{DS}$=drain current, $V_{GS}$=gate-source voltage, $V_T$=threshold voltage, $V_{DS}$=drain-source voltage and K=device transconductance.

Equation (1) can be re-written as:

$$V_{GS} = I_{DS}/(K \cdot V_{DS}) + V_T \quad (2)$$

In FIG. 5, the ISFET is biased with a fixed drain current $I_{DS}$ and fixed drain-source voltage VDS. Since the device transconductance K is a fixed parameter, any variation in threshold voltage $V_T$ will cause a change in the gate-source voltage $V_{GS}$, which is thus measured at the output.

The threshold voltage of an ISFET can be written:

$$V_T = V_{OS} + 2.3 \cdot \alpha \cdot Vth \cdot pH \quad (3)$$

Where Vth=thermal voltage=kT/q, and $V_{OS}$ is a process and chemical-dependent offset voltage which differs from device to device. α is defined as:

$$\alpha = (1 + 2.3 kTC_d/\beta q^2)^{-1} \quad (4)$$

where $C_d$ is the ISFET double layer capacitance which depends on the electrolyte concentration of the sample, and β is the intrinsic buffer capacity of the ISFET gate oxide surface. By choosing a gate oxide material such as $Ta_2O_5$ which exhibits a very high buffer capacity, the value of the second term in equation (4) is negligible, i.e. $2.3 \, kTC_d/\beta q^2 \ll 1$, and thus $\alpha \approx 1$, that is:

$$V_T = V_{OS} + 2.3 \cdot Vth \cdot pH \quad (5)$$

In order to calibrate the ISFET such that changes in pH can be calculated from changes in $V_T$, the offset voltage $V_{OS}$ must be determined. This can be done as follows.

The values of $I_{DS}$ and $V_{DS}$ are fixed by suitable biasing circuitry as shown in FIG. 5. Measurement of $V_{GS}$ thus allows $V_T$ to be determined since K is known from ISFET dimensions and process data. [If K needs to be known with a greater degree of precision, then $I_{DS}$ and/or $V_{DS}$ can be varied allowing two or more measurements of $V_{GS}$ to determine accurate values of both K and $V_T$.]

The value of $V_{OS}$ can be calculated using $V_T$ in equation (5). The thermal voltage $V_{th}$ is known by having a temperature sensor adjacent to the ISFET. If the pH value of the sample is also known, then the value of $V_{OS}$ can be calculated.

As has already been discussed, a fluid sample of known pH can be used to initially calibrate the ISFET. However, it is not practical to do this for every new sensor patch. Thus, it is proposed here to calibrate only a first sensor patch using such a procedure, and thereafter to pass calibration data from one sensor to the next. If a new sensor patch is applied to the user's skin a very short while (say within 5 minutes for blood glucose monitoring) after a previous patch was removed, then it can be assumed that the last pH reading of the previous sensor is still valid and can be used to calibrate the new sensor.

Referring to equation (3) above, the final pH value for the old sensor patch, and a current, measured value of $V_T$ for the new sensor patch can be used to calculate $V_{OS}$ for the new patch. Thereafter, for each successive measurement taken with the new patch, equation (3) can be used to determine the current pH.

Evaluation of equation (3) may be carried out either at the sensor patch 1 or the controller 3 (this will depend upon an evaluation of the trade-off between power consumption due to processing at the patch and power consumption due to the transmission of large data packets over the wireless link). In the case of the former, this will necessitate the sending of the final pH reading for a previous sensor patch, from the controller to the new sensor patch. This exchange might be carried out during a registration process for the new patch with the controller, triggered by powering-up of the new sensor.

Figure 6:
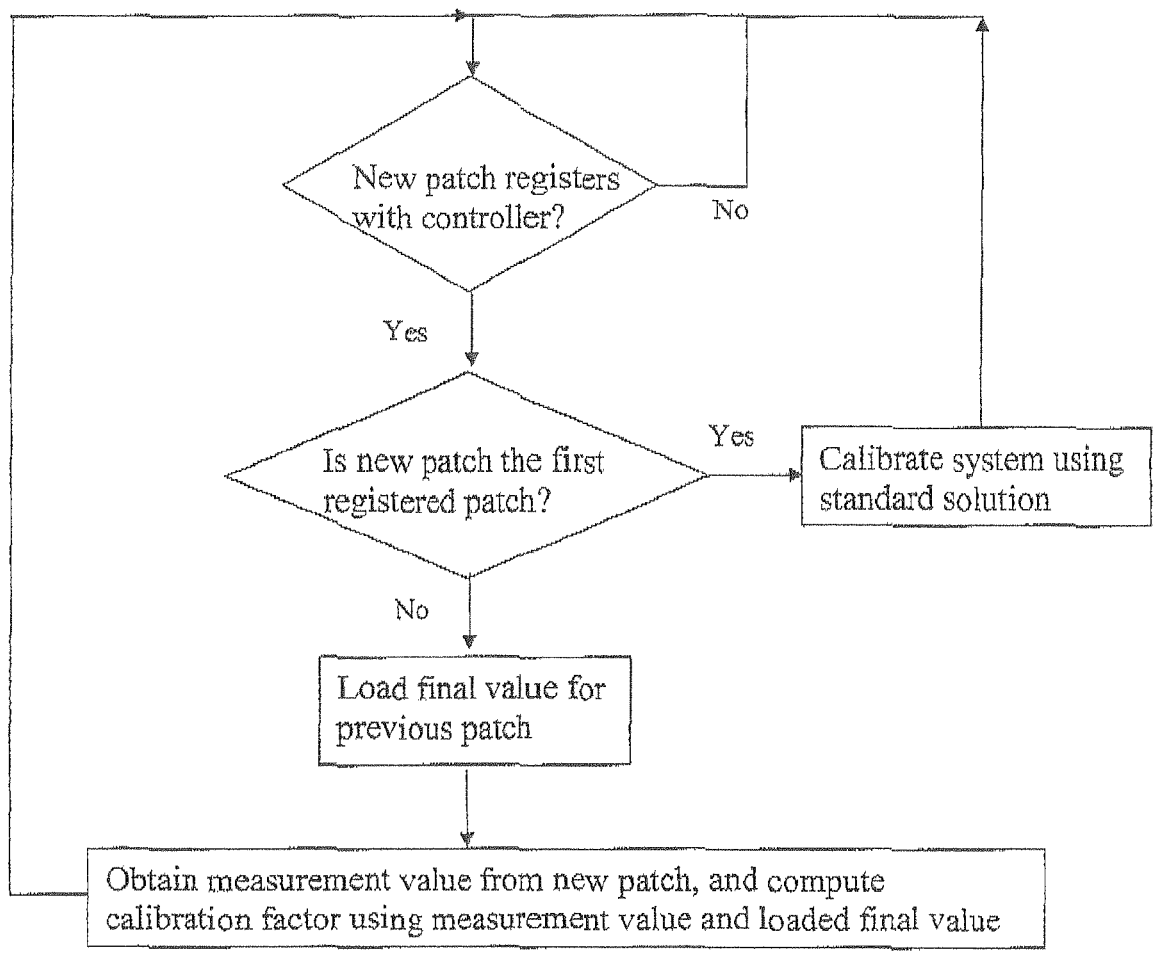
FIG. 6 is a flow diagram illustrating a method of operating the system of FIG. 1.

FIG. 6 is a flow diagram showing the general operating procedure for calibrating the sensor system, each time a new patch is taken into use.

It will be appreciated by the person of skill in the art that various modifications may be made to the above described embodiment without departing from the scope of the present invention. For example, whilst the electronic and electrical components of the patch 1 and controller 3 have been illustrated as discrete functional entities, e.g. processor transceiver, memory, these entities may be merged together, at least to some extent. For example, certain of the functions of the transceiver may be implemented by the processor.

The invention claimed is:

1. A method of calibrating a sensor system comprising a plurality of disposable sensors and a computer device, both the sensors and the computer device having circuitry for facilitating the transmission of data between them via a wireless communication link, the method comprising:
   (a) using a first disposable sensor to monitor a parameter including sending data from the first disposable sensor to said computer device;
   (b) storing a final value of a monitored parameter obtained using said first disposable sensor, or some other value derivable from said final value, in a memory of the computer device, and disposing of said first disposable sensor;
   (c) installing a new disposable sensor including calibrating the sensor system for said new disposable sensor using said final value or said other value and repeating steps a) and b) for the new disposable sensor; and
   d) repeating step c) for each further new disposable sensor.

2. A method according to claim 1 and comprising using said final value or other value to compute a calibration factor for said new or a further new disposable sensor.

3. A method according to claim 2, where said factor is a constant used to evaluate the parameter being monitored from a measured value.

4. A method according to claim 1, wherein the final value or said other value is sent from the computer device to said new or a further new disposable sensor where evaluation of the monitored parameter, or a part of the evaluation, is carried out at the sensor.

5. A method according to claim 1, wherein the final value or said other value is stored at the computer device where evaluation of the monitored parameter, or a part of the evaluation, is carried out.

6. A method according to claim 1, wherein said disposable sensor is wearable.

7. A method according to claim 1, wherein said disposable sensor is a pH sensor.

8. A method according to claim 1, wherein said disposable sensor is an ISFET based biosensor, and the measured value is the gate-source voltage of the ISFET or the voltage or current through the drain/source.

9. A method according to claim 1, wherein the system is arranged in use to determine a blood glucose level.

10. A method according to claim 9, wherein said final value is a blood glucose level.

11. A method according to claim 9, wherein blood glucose level is a function of pH, the pH being derivable from the equation:

$$V_T = V_{os} + 2.3 \cdot \alpha \cdot Vth \cdot pH$$

where Vth=thermal voltage=kT/q, and $V_{os}$ is a process and chemical-dependent offset voltage which differs from sensor to sensor, and α is a temperature and device dependent constant,
   the step of calibrating the system comprising determining $V_{os}$ based upon measurements made with said new or a further new sensor and the final pH value obtained for the first or previous sensor.

12. A method according to claim 1, said step of calibrating the system for said new or a further new disposable sensor being carried out upon power-up of the disposable sensor.

13. A sensor system comprising:
- a plurality of disposable sensors, at least a portion of each sensor being arranged in use to come into contact with a substance; and
- a computer device,
- both the sensor and the computer device having circuitry for facilitating the transmission of data between them via a wireless communication link, the computer device further comprising a memory for storing a final value of a parameter being monitored, or some other value derivable from said final value, for a first disposable sensor, and processing means for using said final or other value to calibrate a second disposable sensor, wherein the computer device is arranged to repeat this procedure for each subsequent disposable sensor using the final value or other value monitored for the previous disposable sensor.

14. A system according to claim 13, the system being arranged in use to determine the blood glucose level of a user.

15. A system according to claim 13, each disposable sensor comprising means for signalling to the computer device that calibration is required, said step of calibrating the system being carried out upon receipt by the computer device of the signalled information.

16. A system according to claim 13, each disposable sensor comprising means for receiving said final value of the parameter being monitored from the computer device over the wireless link.

17. A method according to claim 2, wherein the final value or said other value, or said calibration factor, is sent from the computer device to said new or a further new disposable sensor where evaluation of the monitored parameter, or a part of the evaluation, is carried out at the sensor.

18. A method according to claim 2, wherein the final value or said other value, or said calibration factor, is stored at the computer device where evaluation of the monitored parameter, or a part of the evaluation, is carried out.

* * * * *